United States Patent [19]

Yonezawa

[11] 4,008,259

[45] Feb. 15, 1977

[54] DOUBLE SALTS COPPER ALKYLPHENOLSULFONATE AND BASIC CALCIUM AND METHOD OF PREPARATION

[75] Inventor: Toyozo Yonezawa, Kyoto, Japan

[73] Assignee: Yonezawa Chemical Ind. Co., Ltd., Kyoto, Japan

[22] Filed: Aug. 19, 1975

[21] Appl. No.: 605,923

[52] U.S. Cl. .............................. 260/438.1; 424/294
[51] Int. Cl.$^2$ ........................................... C07F 1/08
[58] Field of Search ................ 424/294; 260/438.1

[56] References Cited

UNITED STATES PATENTS

| 2,864,742 | 12/1958 | Whetstone et al. | 260/438.1 X |
|---|---|---|---|
| 2,897,114 | 7/1959 | Sauls | 424/294 X |
| 3,247,234 | 4/1966 | Ebach | 260/438.1 |
| 3,786,079 | 1/1974 | Yonezawa | 260/438.1 |

OTHER PUBLICATIONS

Chemical Abstracts, V73, 76150 b (1970).

*Primary Examiner*—Helen M. S. Sneed
*Attorney, Agent, or Firm*—Wenderoth, Lind & Ponack

[57] ABSTRACT

Double salts of copper alkylphenolsulfonate and basic calcium are prepared by reacting copper alkylphenolsulfonate having at the para-position an alkyl group of from 4 to 12 carbon atoms and at the ortho-position the sulfonic acid group with basic calcium. The double salts are employed as the effective component of agricultural germicides.

3 Claims, No Drawings

DOUBLE SALTS COPPER ALKYLPHENOLSULFONATE AND BASIC CALCIUM AND METHOD OF PREPARATION

DETAILED DESCRIPTION OF THE INVENTION

This invention relates to agricultural germicides which comprise a double salt of copper alkylphenolsulfonate and basic calcium as their effective component.

Various metal salts of organic acids have been used as an agricultural germicide. Copper, zinc, tin, mercury, nickel, manganese and lead have been used as a salt of aromatic sulfonic acids. In general, however, these salts are disadvantageous and inferior to germicides composed of inorganic double salts of metals in the standpoint of resistance to rain-water and adherence of fixativeness to plants.

As has been recognized, inorganic double salt, such as lime-Bordeaux mixture and various kinds of basic copper double salts, is reacted with carbon dioxide from air and/or with ammonium salts, nitrate and nitrite dissolved in rain-water and converted to water-soluble salt gradually. The water-soluble salts thus formed are adsorbed on spores and/or mycelia of germs thereby to inhibit the SH-enzyme action which takes part in the redox reaction of the living body of the germs. The germs are exterminated by such mechanism. In addition, after the extermination of the germs, the germicide composed of such an inorganic double salt would be able to continue its effect due to its strong resistance to rain-water and can serve as further protection from fresh germs. On the contrary, the germicides composed of metal salt of organic acid, even though they are generally excellent in germicidal effect, are poor in adherence or fixativeness to plants or materials and therefore, tend to be lost when they are exposed to rain. Thus, it can hardly be expected to protect the plants from multiple parasites of fresh germs by single application of the germicides composed of organic acids.

It is therefore an object of the present invention to provide agricultural germicides, comprising a copper salt of organic acid in a form of double salt as the effective constituent, which are excellent not only in germicidal effect but also in resistance to rain-water.

The present inventor has conducted a study of germicides so as to attain the above-mentioned object and found that double salts which are formed by a reaction of basic calcium with copper salts of phenolsulfonic acid derivatives, having at para position an alkyl group containing from 4 to 12 carbon atoms and at ortho position a sulfonic acid group, are excellent in water-resistance and in adherence or fixativeness to plants and are preferable as an agricultural germicide. The present invention is completed on the basis of the findings mentioned above. Other objects and features of the present invention will become apparent in the following description.

The copper salts of phenolsulfonic acid derivatives which are used in the present invention have an alkyl group having from 4 to 12 carbon atoms at para position and a sulfonic acid group at ortho position and are expressed by the following general formula (1), wherein R represents an alkyl group.

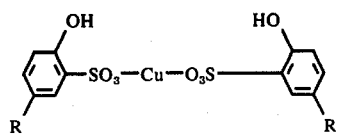

The double salt which is the effective principle of the present germicide is obtained by combining copper alkylphenolsulfonate (1) with calcium hydroxide. Aqueous or methanol solution of the copper alkylphenolsulfonate (1) of about 30% concentration is slowly added with an aqueous suspension of calcium hydroxide to obtain the double salt precipitates. The reaction is expressed by the following equation, wherein $Cu(APS)_2$ represents the copper alkyl phenolsulfonate (1), and when X is equal to 1, Y and Z vary from 0.3–0.6 and 0.05–0.8, respectively in accordance with the variation in the ratio of calcium hydroxide and (1) from 1 to 6 in equivalent.

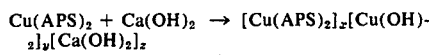

1. Test for resistance of the double salt against water-treatment i. Specimens tested The following seven specimens (listed in Table 1) were prepared and were submitted to the test.

ii. Testing method

One ml of each specimen (listed in Table 1) was dropped and developed uniformly as far as possible on the surface of glass plates having a size of $10 \times 10$ cm², and was followed by drying in air for 24 hours. Each of the glass plates on which the respective specimens were deposited was placed in a vessel filled with water at an angle of 80° and allowed to stand for 2 or 3 hours. The respective glass plates were taken out from the vessel and were washed with 100 ml of methanol. The methanol, respectively collected, was acidified by adding 5 ml of aqueous hydrochloric acid (1 : 4) and then a clear solution was obtained. The content of copper in the respective solution was determined in the usual way according to the colorimetry using sodium diethyl thiocarbamate. The experimental results are summarized in Table 2 in which the results for lime-Bordeaux mixtures are also shown for comparison.

iii. Results

It is obvious from Table 2 that the double salts of copper alkylphenolsulfonate are actually resistant against the water-treatment.

Table 1

| Specimens submitted to test for water-resistance | | | |
|---|---|---|---|
| No. of specimen | Composition of specimen* | | |
| 1 | Copper 4-nonylphenol-2-sulfonate** | 3.1 | g |
|   | Water | 105 | ml |
| 2 | Copper 4-nonylphenol-2-sulfonate** | 3.1 | g |
|   | Calcium hydroxide*** | 0.63 | g |
|   | Water | 125 | ml |
| 3 | Copper 4-nonylphenol-2-sulfonate** | 3.1 | g |
|   | Calcium hydroxide*** | 2.52 | g |

Table 1-continued

| | Specimens submitted to test for water-resistance | | |
|---|---|---|---|
| No. of specimen | Composition of specimen* | | |
| | Water | 125 | ml |
| 4 | Copper 4-butylphenol-2-sulfonate** | 3.1 | g |
| | Water | 105 | ml |
| 5 | Copper 4-butylphenol-2-sulfonate** | 3.1 | g |
| | Calcium hydroxide*** | 2.52 | g |
| | Water | 125 | ml |
| 6 | Copper-4-dodecylphenol-2-sulfonate** | 3.1 | g |
| | Water | 105 | ml |
| 7 | Copper 4-dodecylphenol-2-sulfonate** | 3.1 | g |
| | Calcium hydroxide*** | 2.52 | g |
| | Water | 125 | ml |

*Copper salt was dissolved in 105 ml of water. Calcium hydroxide was suspended in 20 ml of water.
**Used as 30% solution by weight in methanol.
***Commercial calcium hydroxide of 95% purity. The rest is water.

Table 2

| | Results of the water-resistance test. | |
|---|---|---|
| | The amount of copper remaining on the glass plate (%) | |
| No. of specimen | After 2 hours | After 3 hours |
| 1 | 10.0 | 8.3 |
| 2 | 65.7 | 62.4 |
| 3 | 79.6 | 71.3 |
| 4 | 11.0 | 9.2 |
| 5 | 72.3 | 70.2 |
| 6 | 10.5 | 8.4 |
| 7 | 74.2 | 72.6 |
| Lime-Bordeaux (70 liter type) | 90.1 | 87.2 |
| Lime-Bordeaux (108 liter type) | 93.2 | 90.4 |

*On the basis of the total amount of copper deposited on the glass plate.

II. Germicidal performance of the double salt after treatment with water i. Specimens tested The same specimens as those used for the water-resistance test were used.

ii. Testing method

The germicidal effects were tested with respect to water-resistance on a mandarin orange tree (Unshu) in accordance with the leaf blade method as described hereinlater.

A number of sets of young fresh leaves were picked up from a mandarin orange tree and the leaves were cut into five pieces with an uniform size. A number of sets of five pieces of the leaves were immersed for 5 minutes in the respective aqueous solutions of the specimens listed in Table 1 and were withdrawn from the solutions. The leaves were placed on a large piece of filter paper in such a manner that the backside of the leaves were directed upward. After air-drying, the leaves thus treated with the specimens were washed with running water for 1–3 hours and then followed by air-drying. A drop of an aqueous suspension of pycnospores (α-type) of Melanose which contains 150 spores per one fields of microscope (150 times) was placed on the back surface of each of the leaves mentioned above by use of a pipette. The sets of the leaves were placed on a piece of filter paper which were then placed on a piece of wet defatted cotton equipped in a box made of plastics. The respective plastic boxes containing the respective sets of leaves were enveloped in respective sacks formed of polyvinyl chloride and the sacks were placed in a thermostat ranging in temperature from 25°–28° C for 5 days under light irradiation. After 5 days accomodation, the leaves were observed. For reference the leaves which were immersed in the specimens but were not washed were also examined in the same way.

iii. Results

The experimental results are summarized in Table 3.

Table 3

| | Germicidal performance of the double salt | | |
|---|---|---|---|
| | | Washed leaves | |
| No. of specimens | Not-washed leaves | 1 hour washing | 3 hour washing |
| 1 | − | + | + |
| 2 | − | − | − |
| 3 | − | − | ±~− |
| 4 | − | + | + |
| 5 | − | − | − |
| 6 | − | + | + |
| 7 | − | − | ±~− |
| Lime Bordeaux (72 liter type) | − | − | ± |
| Lime-Bordeaux (108 liter type) | − | − | − |
| Mancozeb | − | − | ± |

+ Some disease spots appear.
± Disease spots are hardly observed.
− No disease spots are observed.

It is obvious that the double salts (No. 2, 3, 5 and 7) are effective for the protection of leaves from germs even after the washing with water.

As already described above, the germicides composed of a double salt of copper alkylphenolsulfonate and basic calcium are obviously highly effective and also have a strong resistance against washing with water.

The procedures in which the effective specimens are formed will be demonstrated precisely in the following examples. However, the examples are shown for the purpose of exemplification only and in no way are intended to limit the scope of the invention.

EXAMPLE 1

90 g of copper 4-nonylphenol-2-sulfonate were dissolved in 165 g of water. 19 g of commercial calcium hydroxide (95% purity) were mixed with 180 ml of water and the aqueous suspension thus formed was added to the solution mentioned-above dropwise under continuous agitation at about 50° C. Precipitate was separated and obtained by filtration and then dried. The specimen thus obtained (corresponds to No. 2 in Table 1) was yellowish green in colour and its chemical composition lead to the following experimental formula.

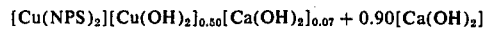

$$[Cu(NPS)_2][Cu(OH)_2]_{0.50}[Ca(OH)_2]_{0.07} + 0.90[Ca(OH)_2]$$

wherein Cu(NPS)$_2$ represents copper 4-nonylphenol-2-sulfonate.

EXAMPLE 2

The procedure for example 1 was repeated except that 76 g of calcium hydroxide were used instead of 19 g. The double salt thus obtained (corresponds to No. 3 in Table 1) was also yellowish green in colour and had the chemical composition which is expressed by the following experimental formula.

$$[Cu(NPS)_2][Cu(OH)_2]_{0.41}[Ca(OH)_2]_{0.71} + 7.50[Ca(OH)_2]$$

The specimens other than the specimens No. 2 and 3 listed in Table 1 were obtained in a similar manner as described above.

I claim:
1. A compound of the formula

$$[Cu(APS)_2]_x[Cu(OH)_2]_y[(Ca)OH)_2]_z$$

wherein Cu(APS)$_2$ represents

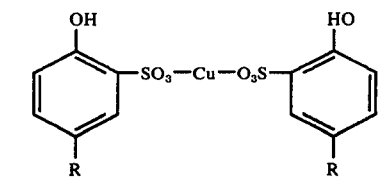

where
R is alkyl of 4 to 12 carbon atoms,
the ratio of Y:X being 0.3–0.6:1, and
the ratio of Z:X being 0.05–0.8:1.

2. A method for the preparation of a double salt of copper alkylphenolsulfonate and basic calcium which comprises reacting an aqueous or methanol solution of copper alkylphenolsulfonate having at the para position an alkyl group of from 4 to 12 carbon atoms and at the ortho position the sulfonic acid group, said solution having a concentration of about 30%, with an aqueous suspension of calcium hydroxide and isolating the thus produced double salt.

3. A method according to claim 2, wherein said copper alkyl phenol sulfonate is copper 4-nonylphenol-2-sulfonate, copper 4-butylphenol-2-sulfonate, or copper 4-dodecylphenol-2-sulfonate.

* * * * *